(12) United States Patent
Möckel et al.

(10) Patent No.: US 6,897,055 B2
(45) Date of Patent: May 24, 2005

(54) NUCLEOTIDE SEQUENCES CODING FOR THE GENES SUCC AND SUCD

(75) Inventors: Bettina Möckel, Düsseldorf (DE); Walter Pfefferle, Halle (DE); Achim Marx, Altenbrede (DE)

(73) Assignee: Degussa AG, Dusseldorf (DE)

( * ) Notice: Subject to any disclaimer, the term of this patent is extended or adjusted under 35 U.S.C. 154(b) by 526 days.

(21) Appl. No.: 09/838,564

(22) Filed: Apr. 20, 2001

(65) Prior Publication Data

US 2002/0072099 A1 Jun. 13, 2002

Related U.S. Application Data

(63) Continuation-in-part of application No. 09/728,498, filed on Nov. 27, 2000.

(30) Foreign Application Priority Data

Nov. 25, 1999 (DE) .......................................... 199 56 686

(51) Int. Cl.$^7$ ................................................. C12N 9/12
(52) U.S. Cl. .................... 435/194; 435/183; 435/252.1; 435/252.3; 435/320.1; 536/23.1
(58) Field of Search ................................ 435/183, 194, 435/252.1, 252.3, 320.1; 536/23.2

(56) References Cited

FOREIGN PATENT DOCUMENTS

| EP | 0 197 335 A | 10/1986 |
|---|---|---|
| WO | 01 00844 A | 1/2001 |

OTHER PUBLICATIONS

Eiglmeier et al. Accession AL035500. Aug. 27, 1999. (Alignment No. 1 and Alignment No. 2).*
Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
Walshaw David L et al: "Regulation of the TCA cycle and the general amino acid permease by overflow metabolism in *Rhizobium leguminosarum*", MICROBIOLOGY Bd. 143, Nr. 7, 1997, p. 2209–2221, XP002163026.
Database EMBL accession: P71558, Nov. 1, 1997, Cole S T et al.: "Succinyl–COA Synthetase Alpha Chain", XP002163027.
Database EMBL accession: P71559, Nov. 1, 1997, Cole S T et al.: "Succinyl–COA Synthetase Beta Chain", XP002163028.
Database EMBL accession: AL035500, Feb. 24, 1999, Harris D et al.: "*Mycobacterium leprae* Cosmid L373", XP002163029.

* cited by examiner

*Primary Examiner*—Ponnathapu Achutamurthy
*Assistant Examiner*—Christian L. Fronda
(74) *Attorney, Agent, or Firm*—Pillsbury Winthrop LLP

(57) ABSTRACT

The invention relates to polynucleotides that contain polynucleotide sequences coding for the genes sucC and sucD, selected from the group a) polynucleotide that is at least 70% identical to a polynucleotide coding for a polypeptide that contains the amino acid sequence of SEQ ID No. 2, b) polynucleotide that is at least 70% identical to a polynucleotide coding for a polypeptide that contains the amino acid sequence of SEQ ID No. 3, c) polynucleotide coding for a polypeptide that contains an amino acid sequence that is at least 70% identical to the amino acid sequence of SEQ ID No. 2, d) polynucleotide coding for a polypeptide that contains an amino acid sequence that is at least 70% identical to the amino acid sequence of SEQ ID No. 3, e) polynucleotide that is complementary to the polynucleotides of a), b), c) or d), and f) polynucleotide containing at least 15 successive nucleotides of the polynucleotide sequence of a), b), c), d) or e), a process for the fermentative production of L-amino acids using coryneform bacteria in which the genes are present in attenuated form, and the use of the polynucleotide sequences as hybridization probes.

20 Claims, 2 Drawing Sheets

Fig. 1: Plasmid pCRBluntsucCint
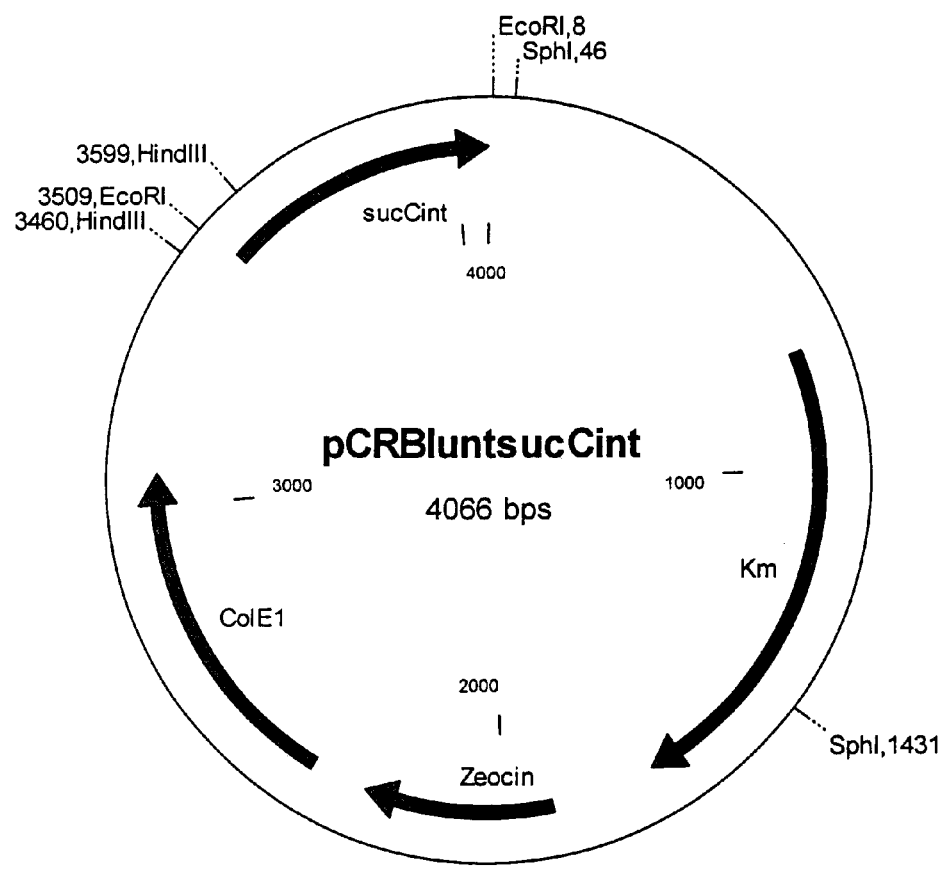

Fig. 2: Plasmid pK18mobsacBsucDdel
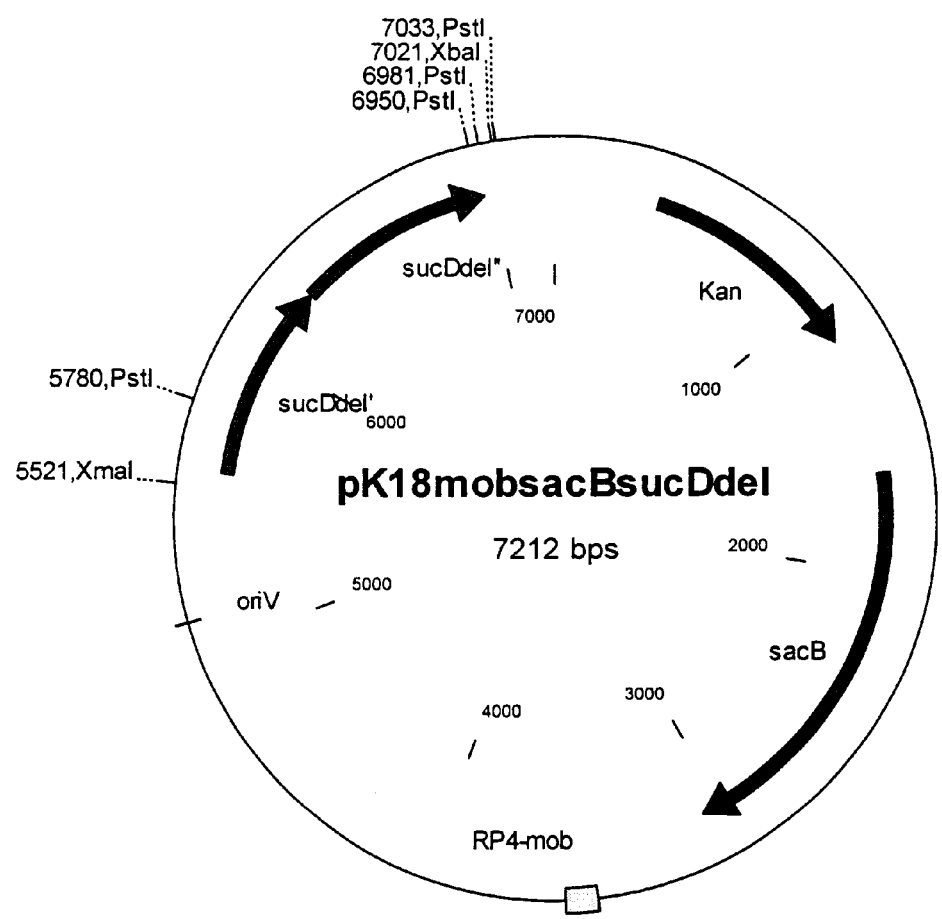

SEQUENCE LISTING

<160> NUMBER OF SEQ ID NOS: 5

<210> SEQ ID NO 1
<211> LENGTH: 2410
<212> TYPE: DNA
<213> ORGANISM: Corynebacterium glutamicum
<220> FEATURE:
<221> NAME/KEY: CDS
<222> LOCATION: (142)..(1347)
<223> OTHER INFORMATION: sucC sequence
<220> FEATURE:
<221> NAME/KEY: CDS
<222> LOCATION: (1372)..(2253)
<223> OTHER INFORMATION: sucD sequence

<400> SEQUENCE: 1

```
gcaccacgga tccaattttg ttgcaatttg caaagtttac agtgttagac ttcacaatac      60
gatcatattg gtgagttgaa acacttactt ttacgggaag actttgttaa agacgcagaa     120
ggctctaagc atgggccgga a atg gaa ttg gca gtg gat ctt ttt gaa tac      171
                       Met Glu Leu Ala Val Asp Leu Phe Glu Tyr
                        1               5                  10 caa gca cgg gac ctc ttt gaa acc cat ggt gtg cca gtg ttg aag gga      219
Gln Ala Arg Asp Leu Phe Glu Thr His Gly Val Pro Val Leu Lys Gly
             15                  20                  25 att gtg gca tca aca cca gag gcg gcg agg aaa gcg gct gag gaa atc      267
Ile Val Ala Ser Thr Pro Glu Ala Ala Arg Lys Ala Ala Glu Glu Ile
         30                  35                  40 ggc gga ctg acc gtc gtc aag gct cag gtc aag gtg ggc gga cgt ggc      315
Gly Gly Leu Thr Val Val Lys Ala Gln Val Lys Val Gly Gly Arg Gly
     45                  50                  55 aag gcg ggt ggc gtc cgt gtg gca ccg acg tcg gct cag gct ttt          363
Lys Ala Gly Gly Val Arg Val Ala Pro Thr Ser Ala Gln Ala Phe Asp
 60                  65                  70 gct gcg gat gcg att ctc ggc atg gat atc aaa gga cac act gtt aat      411
Ala Ala Asp Ala Ile Leu Gly Met Asp Ile Lys Gly His Thr Val Asn
75                  80                  85                  90 cag gtg atg gtg gcg cag ggc gct gac att gct gag gaa tac tat ttc      459
Gln Val Met Val Ala Gln Gly Ala Asp Ile Ala Glu Glu Tyr Tyr Phe
                 95                 100                 105 tcc att ttg ttg gat cgc gcg aat cgt tcg tat ctg gct atg tgc tct      507
Ser Ile Leu Leu Asp Arg Ala Asn Arg Ser Tyr Leu Ala Met Cys Ser
             110                 115                 120 gtt gaa ggt ggc atg gag atc gag atc ctg gcg aag gaa aag cct gaa      555
Val Glu Gly Gly Met Glu Ile Glu Ile Leu Ala Lys Glu Lys Pro Glu
         125                 130                 135 gct ttg gca aag gtg gaa gtg gat ccc ctc act ggt att gat gag gac      603
Ala Leu Ala Lys Val Glu Val Asp Pro Leu Thr Gly Ile Asp Glu Asp
     140                 145                 150 aaa gcg cgg gag att gtc act gct gct ggc ttt gaa act gag gtg gca      651
Lys Ala Arg Glu Ile Val Thr Ala Ala Gly Phe Glu Thr Glu Val Ala
155                 160                 165                 170 gag aaa gtc att ccg gtg ctg atc aag atc tgg cag gtg tat tac gaa      699
Glu Lys Val Ile Pro Val Leu Ile Lys Ile Trp Gln Val Tyr Tyr Glu
                175                 180                 185 gag gaa gca aca ctc gtt gag gtg aac ccg ttg gtg ctc acg gat gac      747
Glu Glu Ala Thr Leu Val Glu Val Asn Pro Leu Val Leu Thr Asp Asp
            190                 195                 200 ggc gat gtg att gcg ctt gat ggc aag atc acg ctg gat gat aac gct      795
```

```
          Gly Asp Val Ile Ala Leu Asp Gly Lys Ile Thr Leu Asp Asp Asn Ala
                      205                 210                 215 gat ttc cgc cat gat aac cgt ggt gcg ttg gct gaa tct gcc ggt ggc        843
Asp Phe Arg His Asp Asn Arg Gly Ala Leu Ala Glu Ser Ala Gly Gly
220                 225                 230 ttg gac att ttg gaa ctg aag gcc aag aag aat gat ctg aac tac gtg        891
Leu Asp Ile Leu Glu Leu Lys Ala Lys Lys Asn Asp Leu Asn Tyr Val
235                 240                 245                 250 aaa ctt gat ggc tct gtg ggc atc att ggc aat ggt gca ggt ttg gtg        939
Lys Leu Asp Gly Ser Val Gly Ile Ile Gly Asn Gly Ala Gly Leu Val
                    255                 260                 265 atg tcc acg ttg gat atc gtg gct gca gct ggt gaa cgc cat ggt ggg        987
Met Ser Thr Leu Asp Ile Val Ala Ala Ala Gly Glu Arg His Gly Gly
                    270                 275                 280 cag cgc ccc gcg aac ttc cta gac att ggt ggc gga gca tca gct gaa       1035
Gln Arg Pro Ala Asn Phe Leu Asp Ile Gly Gly Gly Ala Ser Ala Glu
                285                 290                 295 tcg atg gct gct ggt ctc gat gtg atc ctt ggg gat agc cag gta cgc       1083
Ser Met Ala Ala Gly Leu Asp Val Ile Leu Gly Asp Ser Gln Val Arg
300                 305                 310 agt gtg ttt gtg aat gtg ttt ggt ggc atc acc gcg tgt gat gtg gtg       1131
Ser Val Phe Val Asn Val Phe Gly Gly Ile Thr Ala Cys Asp Val Val
315                 320                 325                 330 gca aag gga atc gtt gga gct ttg gat gtg ctc ggc gat caa gca acg       1179
Ala Lys Gly Ile Val Gly Ala Leu Asp Val Leu Gly Asp Gln Ala Thr
                    335                 340                 345 aag cct ctt gtg gtg cgc ctt gat ggc aac aac gtg gtg gaa ggc aga       1227
Lys Pro Leu Val Val Arg Leu Asp Gly Asn Asn Val Val Glu Gly Arg
                350                 355                 360 cga atc ctc gcg gaa tat aac cac cct ttg gtc acc gtt gtg gag ggt       1275
Arg Ile Leu Ala Glu Tyr Asn His Pro Leu Val Thr Val Val Glu Gly
            365                 370                 375 atg gat gca gcg gct gat cac gct gcc cat ttg gcc aat ctt gcc cag       1323
Met Asp Ala Ala Ala Asp His Ala Ala His Leu Ala Asn Leu Ala Gln
380                 385                 390 cac ggc cag ttc gca acc gct aat tagttaagga gcacctgttt aatc atg        1374
His Gly Gln Phe Ala Thr Ala Asn                                  Met
395                 400 tct att ttt ctc aat tca gat tcc cgc atc atc att cag ggc att acc       1422
Ser Ile Phe Leu Asn Ser Asp Ser Arg Ile Ile Ile Gln Gly Ile Thr
        405                 410                 415 ggt tcg gaa ggt tca gag cat gcg cgt cga att tta gcc tct ggt gcg       1470
Gly Ser Glu Gly Ser Glu His Ala Arg Arg Ile Leu Ala Ser Gly Ala
420                 425                 430                 435 aag ctc gtg ggt ggc acc aac ccc cgc aaa gct ggg caa acc att ttg       1518
Lys Leu Val Gly Gly Thr Asn Pro Arg Lys Ala Gly Gln Thr Ile Leu
                440                 445                 450 atc aat gac act gag ttg cct gta ttt ggc act gtt aag gaa gca atg       1566
Ile Asn Asp Thr Glu Leu Pro Val Phe Gly Thr Val Lys Glu Ala Met
            455                 460                 465 gag gaa acg ggt gcg gat gtc acc gta att ttc gtt cct cca gcc ttt       1614
Glu Glu Thr Gly Ala Asp Val Thr Val Ile Phe Val Pro Pro Ala Phe
        470                 475                 480 gcc aaa gct gcg atc att gaa gct atc gac gct cac atc cca ctg tgc       1662
Ala Lys Ala Ala Ile Ile Glu Ala Ile Asp Ala His Ile Pro Leu Cys
    485                 490                 495 gtg att att act gag ggc atc cca gtg cgt gac gct tct gag gcg tgg       1710
Val Ile Ile Thr Glu Gly Ile Pro Val Arg Asp Ala Ser Glu Ala Trp
500                 505                 510                 515
```

-continued

```
gct tat gcc aag aag gtg gga cac acc cgc atc att ggc cct aac tgc      1758
Ala Tyr Ala Lys Lys Val Gly His Thr Arg Ile Ile Gly Pro Asn Cys
            520                 525                 530 cca ggc att att act ccc ggc gaa tct ctt gcg gga att acg ccg gca      1806
Pro Gly Ile Ile Thr Pro Gly Glu Ser Leu Ala Gly Ile Thr Pro Ala
        535                 540                 545 aac att gca ggt tcc ggc ccg atc ggg ttg atc tca aag tcg gga aca      1854
Asn Ile Ala Gly Ser Gly Pro Ile Gly Leu Ile Ser Lys Ser Gly Thr
        550                 555                 560 ctg act tat cag atg atg tac gaa ctt tca gat att ggc att tct acg      1902
Leu Thr Tyr Gln Met Met Tyr Glu Leu Ser Asp Ile Gly Ile Ser Thr
    565                 570                 575 gcg att ggt att ggc ggt gac cca atc atc ggt aca acc cat atc gac      1950
Ala Ile Gly Ile Gly Gly Asp Pro Ile Ile Gly Thr Thr His Ile Asp
580                 585                 590                 595 gct ctg gag gcc ttt gaa gca gat cct gag acc aag gca atc gtc atg      1998
Ala Leu Glu Ala Phe Glu Ala Asp Pro Glu Thr Lys Ala Ile Val Met
                600                 605                 610 atc ggt gag atc ggt gga gat gca gag gaa cgc gct gct gac ttc att      2046
Ile Gly Glu Ile Gly Gly Asp Ala Glu Glu Arg Ala Ala Asp Phe Ile
            615                 620                 625 tct aag cac gtg aca aaa cca gtt gtg ggt tac gtg gca ggc ttt acc      2094
Ser Lys His Val Thr Lys Pro Val Val Gly Tyr Val Ala Gly Phe Thr
        630                 635                 640 gcc cct gaa gga aag acc atg ggg cat gct ggc gcc atc gtg aca ggt      2142
Ala Pro Glu Gly Lys Thr Met Gly His Ala Gly Ala Ile Val Thr Gly
    645                 650                 655 tca gaa ggc act gcg cga gca aag aag cat gca ttg gag gcc gtg ggt      2190
Ser Glu Gly Thr Ala Arg Ala Lys Lys His Ala Leu Glu Ala Val Gly
660                 665                 670                 675 gtt cgc gtg gga aca act ccg agt gaa acc gcg aag ctt atg cgt gag      2238
Val Arg Val Gly Thr Thr Pro Ser Glu Thr Ala Lys Leu Met Arg Glu
                680                 685                 690 gta gtt gca gct ttg taactaacag gccacagatc ttagctttga ccagcggatt     2293
Val Val Ala Ala Leu
            695 tgtggctaat cgcccggtct gtgtagagta ttcatctgtg cgcaggacag tgtgacaaac    2353 actgaatagt gcatggcttt aaggccctgt ggcgcagttg gttagcgcgc cgccctg       2410
```

<210> SEQ ID NO 2
<211> LENGTH: 402
<212> TYPE: PRT
<213> ORGANISM: Corynebacterium glutamicum

<400> SEQUENCE: 2

```
Met Glu Leu Ala Val Asp Leu Phe Glu Tyr Gln Ala Arg Asp Leu Phe
1               5                   10                  15

Glu Thr His Gly Val Pro Val Leu Lys Gly Ile Val Ala Ser Thr Pro
            20                  25                  30

Glu Ala Ala Arg Lys Ala Ala Glu Glu Ile Gly Gly Leu Thr Val Val
        35                  40                  45

Lys Ala Gln Val Lys Val Gly Gly Arg Gly Lys Ala Gly Gly Val Arg
    50                  55                  60

Val Ala Pro Thr Ser Ala Gln Ala Phe Asp Ala Asp Ala Ile Leu
65                  70                  75                  80

Gly Met Asp Ile Lys Gly His Thr Val Asn Gln Val Met Val Ala Gln
                85                  90                  95
```

```
Gly Ala Asp Ile Ala Glu Glu Tyr Tyr Phe Ser Ile Leu Leu Asp Arg
            100                 105                 110

Ala Asn Arg Ser Tyr Leu Ala Met Cys Ser Val Glu Gly Met Glu
        115                 120                 125

Ile Glu Ile Leu Ala Lys Glu Lys Pro Glu Ala Leu Ala Lys Val Glu
    130                 135                 140

Val Asp Pro Leu Thr Gly Ile Asp Glu Asp Lys Ala Arg Glu Ile Val
145                 150                 155                 160

Thr Ala Ala Gly Phe Glu Thr Glu Val Ala Glu Lys Val Ile Pro Val
                165                 170                 175

Leu Ile Lys Ile Trp Gln Val Tyr Tyr Glu Glu Ala Thr Leu Val
            180                 185                 190

Glu Val Asn Pro Leu Val Leu Thr Asp Asp Gly Asp Val Ile Ala Leu
        195                 200                 205

Asp Gly Lys Ile Thr Leu Asp Asp Asn Ala Asp Phe Arg His Asp Asn
    210                 215                 220

Arg Gly Ala Leu Ala Glu Ser Ala Gly Gly Leu Asp Ile Leu Glu Leu
225                 230                 235                 240

Lys Ala Lys Lys Asn Asp Leu Asn Tyr Val Lys Leu Asp Gly Ser Val
                245                 250                 255

Gly Ile Ile Gly Asn Gly Ala Gly Leu Val Met Ser Thr Leu Asp Ile
            260                 265                 270

Val Ala Ala Gly Glu Arg His Gly Gly Gln Arg Pro Ala Asn Phe
        275                 280                 285

Leu Asp Ile Gly Gly Gly Ala Ser Ala Glu Ser Met Ala Ala Gly Leu
    290                 295                 300

Asp Val Ile Leu Gly Asp Ser Gln Val Arg Ser Val Phe Val Asn Val
305                 310                 315                 320

Phe Gly Gly Ile Thr Ala Cys Asp Val Ala Lys Gly Ile Val Gly
                325                 330                 335

Ala Leu Asp Val Leu Gly Asp Gln Ala Thr Lys Pro Leu Val Val Arg
            340                 345                 350

Leu Asp Gly Asn Asn Val Val Glu Gly Arg Arg Ile Leu Ala Glu Tyr
        355                 360                 365

Asn His Pro Leu Val Thr Val Val Glu Gly Met Asp Ala Ala Ala Asp
    370                 375                 380

His Ala Ala His Leu Ala Asn Leu Ala Gln His Gly Gln Phe Ala Thr
385                 390                 395                 400

Ala Asn

SEQ ID NO 3
<211> LENGTH: 294
<212> TYPE: PRT
<213> ORGANISM: Corynebacterium glutamicum

<400> SEQUENCE: 3

Met Ser Ile Phe Leu Asn Ser Asp Ser Arg Ile Ile Gln Gly Ile
1               5                   10                  15

Thr Gly Ser Glu Gly Ser Glu His Ala Arg Arg Ile Leu Ala Ser Gly
            20                  25                  30

Ala Lys Leu Val Gly Gly Thr Asn Pro Arg Lys Ala Gly Gln Thr Ile
        35                  40                  45

Leu Ile Asn Asp Thr Glu Leu Pro Val Phe Gly Thr Val Lys Glu Ala
    50                  55                  60
```

```
Met Glu Glu Thr Gly Ala Asp Val Thr Val Ile Phe Val Pro Pro Ala
 65                  70                  75                  80

Phe Ala Lys Ala Ala Ile Ile Glu Ala Ile Asp Ala His Ile Pro Leu
                 85                  90                  95

Cys Val Ile Ile Thr Glu Gly Ile Pro Val Arg Asp Ala Ser Glu Ala
            100                 105                 110

Trp Ala Tyr Ala Lys Lys Val Gly His Thr Arg Ile Ile Gly Pro Asn
        115                 120                 125

Cys Pro Gly Ile Ile Thr Pro Gly Glu Ser Leu Ala Gly Ile Thr Pro
    130                 135                 140

Ala Asn Ile Ala Gly Ser Gly Pro Ile Gly Leu Ile Ser Lys Ser Gly
145                 150                 155                 160

Thr Leu Thr Tyr Gln Met Met Tyr Glu Leu Ser Asp Ile Gly Ile Ser
                165                 170                 175

Thr Ala Ile Gly Ile Gly Gly Asp Pro Ile Ile Gly Thr Thr His Ile
            180                 185                 190

Asp Ala Leu Glu Ala Phe Glu Ala Asp Pro Glu Thr Lys Ala Ile Val
        195                 200                 205

Met Ile Gly Glu Ile Gly Gly Asp Ala Glu Arg Ala Ala Asp Phe
    210                 215                 220

Ile Ser Lys His Val Thr Lys Pro Val Val Gly Tyr Val Ala Gly Phe
225                 230                 235                 240

Thr Ala Pro Glu Gly Lys Thr Met Gly His Ala Gly Ala Ile Val Thr
                245                 250                 255

Gly Ser Glu Gly Thr Ala Arg Ala Lys Lys His Ala Leu Glu Ala Val
            260                 265                 270

Gly Val Arg Val Gly Thr Thr Pro Ser Glu Thr Ala Lys Leu Met Arg
        275                 280                 285

Glu Val Val Ala Ala Leu
    290

<210> SEQ ID NO 4
<211> LENGTH: 1206
<212> TYPE: DNA
<213> ORGANISM: Corynebacterium glutamicum
<220> FEATURE:
<221> NAME/KEY: CDS
<222> LOCATION: (1)..(1206)
<223> OTHER INFORMATION: sucC coding sequence

<400> SEQUENCE: 4 atg gaa ttg gca gtg gat ctt ttt gaa tac caa gca cgg gac ctc ttt      48
Met Glu Leu Ala Val Asp Leu Phe Glu Tyr Gln Ala Arg Asp Leu Phe
1               5                   10                  15 gaa acc cat ggt gtg tca gtg ttg aag gga att gtg gca tca aca cca      96
Glu Thr His Gly Val Ser Val Leu Lys Gly Ile Val Ala Ser Thr Pro
            20                  25                  30 gag gcg gcg agg aaa gcg gct gag gaa atc ggc gaa ctg acc gtc gtc     144
Glu Ala Ala Arg Lys Ala Ala Glu Glu Ile Gly Glu Leu Thr Val Val
        35                  40                  45 aag gct cag gtc aag gtg ggc gga cgt ggc aag gcg ggt ggc gtc cgt     192
Lys Ala Gln Val Lys Val Gly Gly Arg Gly Lys Ala Gly Gly Val Arg
    50                  55                  60 gtg gca ccg acg tcg gct cag gct ttt gat gct gcg gat gcg att ctc     240
Val Ala Pro Thr Ser Ala Gln Ala Phe Asp Ala Ala Asp Ala Ile Leu
65                  70                  75                  80 ggc atg gat atc aaa gga cac act gtt aat cag gtg atg gtg gcg cag     288
```

```
                                     Gly Met Asp Ile Lys Gly His Thr Val Asn Gln Val Met Val Ala Gln
                                                     85                  90                  95 ggc gct gac att gct gag gaa tac tat ttc tcc att ttg ttg gat cgc          336
Gly Ala Asp Ile Ala Glu Glu Tyr Tyr Phe Ser Ile Leu Leu Asp Arg
            100                 105                 110 gcg aat cgt tcg tat ctg gct atg tgc tct gtt gaa ggt ggc atg gag          384
Ala Asn Arg Ser Tyr Leu Ala Met Cys Ser Val Glu Gly Gly Met Glu
        115                 120                 125 atc gag atc ctg gcg aag gaa aag cct gaa gct ttg gca aag gtg gaa          432
Ile Glu Ile Leu Ala Lys Glu Lys Pro Glu Ala Leu Ala Lys Val Glu
130                 135                 140 gtg gat ccc ctc act ggt att gat gag gac aaa gcg cgg gag att gtc          480
Val Asp Pro Leu Thr Gly Ile Asp Glu Asp Lys Ala Arg Glu Ile Val
145                 150                 155                 160 act gct gct ggc ttt gaa act gag gtg aca gag aaa gtc att ccg gtg          528
Thr Ala Ala Gly Phe Glu Thr Glu Val Thr Glu Lys Val Ile Pro Val
                165                 170                 175 ctg atc aag atc tgg cag gtg tat tac gaa gag gaa gca aca ctc gtt          576
Leu Ile Lys Ile Trp Gln Val Tyr Tyr Glu Glu Glu Ala Thr Leu Val
            180                 185                 190 gag gtg aac ccg ttg gtg ctc acg gat gac ggc gat gtg att gcg ctt          624
Glu Val Asn Pro Leu Val Leu Thr Asp Asp Gly Asp Val Ile Ala Leu
        195                 200                 205 gat ggc aag atc acg ctg gat gat aac gct gat ttc cgc cat gat aac          672
Asp Gly Lys Ile Thr Leu Asp Asp Asn Ala Asp Phe Arg His Asp Asn
210                 215                 220 cgt ggt gcg ttg gct gaa tct gcc ggt ggc ttg gac att ttg gaa ctg          720
Arg Gly Ala Leu Ala Glu Ser Ala Gly Gly Leu Asp Ile Leu Glu Leu
225                 230                 235                 240 aag gcc aag aag aat gat ctg aac tac gtg aaa ctt gat ggc tct gtg          768
Lys Ala Lys Lys Asn Asp Leu Asn Tyr Val Lys Leu Asp Gly Ser Val
                245                 250                 255 ggc atc att ggc aat ggt gca ggt ttg gtg atg tcc acg ttg gat atc          816
Gly Ile Ile Gly Asn Gly Ala Gly Leu Val Met Ser Thr Leu Asp Ile
            260                 265                 270 gtg gct gca gct ggt gaa cgc cat ggt ggg cag cgc ccc gcg aac ttc          864
Val Ala Ala Ala Gly Glu Arg His Gly Gly Gln Arg Pro Ala Asn Phe
        275                 280                 285 cta gac att ggt ggc gga gca tca gct gaa tcg atg gct gct ggt ctc          912
Leu Asp Ile Gly Gly Gly Ala Ser Ala Glu Ser Met Ala Ala Gly Leu
290                 295                 300 gat gtg atc ctt ggg gat agc cag gta cgc agt gtg ttt gtg aat gtg          960
Asp Val Ile Leu Gly Asp Ser Gln Val Arg Ser Val Phe Val Asn Val
305                 310                 315                 320 ttt ggt ggc atc acc gcg tgt gat gtg gtg gca aag gga atc gtt gga         1008
Phe Gly Gly Ile Thr Ala Cys Asp Val Val Ala Lys Gly Ile Val Gly
                325                 330                 335 gct ttg gat gtg ctc ggc gat caa gca acg aag cct ctt gtg gtg cgc         1056
Ala Leu Asp Val Leu Gly Asp Gln Ala Thr Lys Pro Leu Val Val Arg
            340                 345                 350 ctt gat ggc aac aac gtg gtg gaa ggc aga cga atc ctc gcg gaa tat         1104
Leu Asp Gly Asn Asn Val Val Glu Gly Arg Arg Ile Leu Ala Glu Tyr
        355                 360                 365 aac cac cct ttg gtc acc gtt gtg gag ggt atg gat gca gcg gct gat         1152
Asn His Pro Leu Val Thr Val Val Glu Gly Met Asp Ala Ala Ala Asp
370                 375                 380 cac gct gcc cat ttg gcc aat ctt gcc cag cac ggc cag ttc gca acc         1200
His Ala Ala His Leu Ala Asn Leu Ala Gln His Gly Gln Phe Ala Thr
385                 390                 395                 400
```

```
gct aat                                                              1206
Ala Asn
```

<210> SEQ ID NO 5
<211> LENGTH: 402
<212> TYPE: PRT
<213> ORGANISM: Corynebacterium glutamicum

<400> SEQUENCE: 5

```
Met Glu Leu Ala Val Asp Leu Phe Glu Tyr Gln Ala Arg Asp Leu Phe
1               5                   10                  15

Glu Thr His Gly Val Ser Val Leu Lys Gly Ile Val Ala Ser Thr Pro
            20                  25                  30

Glu Ala Ala Arg Lys Ala Ala Glu Ile Gly Glu Leu Thr Val Val
        35                  40                  45

Lys Ala Gln Val Lys Val Gly Gly Arg Gly Lys Ala Gly Gly Val Arg
50                  55                  60

Val Ala Pro Thr Ser Ala Gln Ala Phe Asp Ala Ala Asp Ala Ile Leu
65                  70                  75                  80

Gly Met Asp Ile Lys Gly His Thr Val Asn Gln Val Met Val Ala Gln
                85                  90                  95

Gly Ala Asp Ile Ala Glu Glu Tyr Tyr Phe Ser Ile Leu Leu Asp Arg
            100                 105                 110

Ala Asn Arg Ser Tyr Leu Ala Met Cys Ser Val Glu Gly Gly Met Glu
        115                 120                 125

Ile Glu Ile Leu Ala Lys Glu Lys Pro Glu Ala Leu Ala Lys Val Glu
130                 135                 140

Val Asp Pro Leu Thr Gly Ile Asp Glu Asp Lys Ala Arg Glu Ile Val
145                 150                 155                 160

Thr Ala Ala Gly Phe Glu Thr Glu Val Thr Glu Lys Val Ile Pro Val
                165                 170                 175

Leu Ile Lys Ile Trp Gln Val Tyr Tyr Glu Glu Ala Thr Leu Val
            180                 185                 190

Glu Val Asn Pro Leu Val Leu Thr Asp Asp Gly Asp Val Ile Ala Leu
        195                 200                 205

Asp Gly Lys Ile Thr Leu Asp Asp Asn Ala Asp Phe Arg His Asp Asn
210                 215                 220

Arg Gly Ala Leu Ala Glu Ser Ala Gly Gly Leu Asp Ile Leu Glu Leu
225                 230                 235                 240

Lys Ala Lys Lys Asn Asp Leu Asn Tyr Val Lys Leu Asp Gly Ser Val
                245                 250                 255

Gly Ile Ile Gly Asn Gly Ala Gly Leu Val Met Ser Thr Leu Asp Ile
            260                 265                 270

Val Ala Ala Gly Glu Arg His Gly Gly Gln Arg Pro Ala Asn Phe
        275                 280                 285

Leu Asp Ile Gly Gly Gly Ala Ser Ala Glu Ser Met Ala Ala Gly Leu
290                 295                 300

Asp Val Ile Leu Gly Asp Ser Gln Val Arg Ser Val Phe Val Asn Val
305                 310                 315                 320

Phe Gly Gly Ile Thr Ala Cys Asp Val Val Lys Gly Ile Val Gly
                325                 330                 335

Ala Leu Asp Val Leu Gly Asp Gln Ala Thr Lys Pro Leu Val Val Arg
            340                 345                 350

Leu Asp Gly Asn Asn Val Val Glu Gly Arg Arg Ile Leu Ala Glu Tyr
```

-continued

```
              355                 360                 365
Asn His Pro Leu Val Thr Val Val Glu Gly Met Asp Ala Ala Asp
    370                 375                 380

His Ala Ala His Leu Ala Asn Leu Ala Gln His Gly Gln Phe Ala Thr
385                 390                 395                 400

Ala Asn
```

NUCLEOTIDE SEQUENCES CODING FOR THE GENES SUCC AND SUCD

CROSS REFERENCE TO RELATED APPLICATIONS

The present application is a continuation-in-part 35 U.S.C. §120 to U.S. application Ser. No. 09/728,498 filed on Nov. 27, 2000. Priority is also claimed under 35 U.S.C. §119 to German application 199 56 686 0 filed on Nov. 25, 1999.

The present invention provides nucleotide sequences of coryneform bacteria coding for the genes sucC and sucD and a process for the fermentative production of amino acids, in particular L-lysine and L-glutamate, using bacteria in which the sucC- and/or sucD-gene is/are attenuated.

PRIOR ART

L-amino acids, in particular L-lysine and L-glutamate, are used in human medicine and in the pharmaceutical industry, in the foodstuffs industry, and most particularly in animal nutrition.

It is known that amino acids can be produced by fermentation of strains of coryneform bacteria, in particular *Corynebacterium glutamicum* (*C. glutamicum*). On account of the great importance of amino acids efforts are constantly being made to improve the production processes. Improvements in production may involve fermentation technology measures, such as for example stirring and provision of oxygen, or the composition of the nutrient media, such as for example the sugar concentration during fermentation or the working-up to the product form by, for example, ion exchange chromatography, or the intrinsic output properties of the microorganism itself.

Methods involving mutagenesis, selection and choice of mutants are used to improve the output properties. In this way strains are obtained that are resistant to antimetabolites or are auxotrophic for regulatorily important metabolites, and that produce amino acids.

For some years recombinant DNA technology methods have also beer used to improve Corynebacterium strains producing L-amino acids.

OBJECTION OF THE INVENTION

The inventors have set themselves the task of providing new measures for improving the fermentative production of amino acids, in particular L-lysine and L-glutamate.

DETAILED DESCRIPTION OF THE INVENTION

Where L-amino acids or amino acids are mentioned hereinafter, it is understood that these terms refer to one or more amino acids, including their salts, selected from the group comprising L-asparagine, L-threonine, L-serine, L-glutamate, L-glycine, L-alanine, L-cysteine, L-valine, L-methhonine, L-isoleucine, L-leucine, L-tyrosine, L-phenylalanine, L-histidine, L-lysine, L-tryptophan and L-arginine. L-lysine and L-glutamate are particularly preferred.

The present invention provides an isolated polynucleotide containing a polynucleotide sequence selected from the group comprising a) polynucleotide that is at least 70% identical to a polynucleotide coding for a polypeptide, that contains the amino acid sequence of SEQ ID No. 2, b) polynucleotide that is at least 70% identical to a polynucleotide coding for a polypeptide, that contains the amino acid sequence of SEQ ID No. 3, c) polynucleotide coding for a polypeptide, that contains an amino acid sequence that is at least 70% identical to the amino acid sequence of SEQ ID No. 2, d) polynucleotide coding for a polypeptide, that contains an amino acid sequence that is at least 70% identical to the amino acid sequence of SEQ ID No. 3, e) polynucleotide that is complementary to the polynucleotides of a), b), c) or d), and f) polynucleotide containing at least 15 successive nucleotides of the polynucleotide sequence of a), b), c), d) or e), the polypeptide preferably exhibiting the activity of succinyl-CoA synthetase.

The present invention also provides the polynucleotide according to claim 1, which is preferably a replicable DNA containing:

(i) the nucleotide sequence shown in SEQ ID No. 1, or (ii) at least one sequence that corresponds to the sequence (i) within the region of degeneration of the genetic code, or (iii) at least one sequence that hybridizes with the sequence complementary to the sequence (i) or (ii), and optionally (iv) functionally neutral sense mutations in (i).

The invention furthermore provides:

a polynucleotide according to claim 4, containing the nucleotide sequence as shown in SEQ ID No. 1, a polynucleotide according to claim 1, wherein the polynucleotide is a preferably recombinant DNA replicable in coryneform bacteria, a vector containing parts of the polynucleotide according to the invention, but at least 15 successive nucleotides of the claimed sequence, and coryneform bacteria in which the sucC- and/or sucD-gene is/are attenuated in particular by an insertion or deletion.

The present invention moreover provides polynucleotides that substantially comprise a polynucleotide sequence, that can be obtained by screening a corresponding gene library by means of hybridization, that contains the complete sucC- and/or sucD-gene with the polynucleotide sequence corresponding to SEQ ID No. 1 with a probe that contains the sequence of the aforementioned polynucleotide according to SEQ ID No. 1 or a fragment thereof, and isolation of the aforementioned DNA sequence.

Polynucleotides that contain the sequences according to the invention are suitable as hybridization probes for RNA, cDNA and DNA, in order to isolate cDNA, nucleic acids and/or polynucleotides or genes in their full length that code for succinyl-CoA synthetase, and to isolate such cDNA or genes whose sequence has a high similarity to that of the succinyl-CoA synthetase genes.

Polyriucleotides that contain the sequences according to the invention are furthermore suitable as primers, by means of which DNA can be produced by the polymerase chain reaction (PCR) from genes that code for succinyl-CoA synthetase.

Such oligonucleotides serving as probes or primers contain at least 30, preferably at least 20, and most particularly preferably at least 15 successive nucleotides. Nucleotides with a length of at least 40 or 50 nucleotides are also suitable.

"Isolated" means separated from its natural environment.

"Polynucleotide" refers in general to polyribonucleotides and polydeoxyribonucleotides, in which connection these terms may refer to unmodified RNA or DNA or modified RNA or DNA.

By the term "polypeptides" are understood peptides or proteains that contain two or more amino acids bound via peptide bonds.

The polypeptides according to the invention include the polypeptides according to SEQ ID No. 2 and SEQ ID No. 3, in particular those having the biological activity of succinyl-CoA synthetase as well as those that are at least 70% identical to the polypeptide according to SEQ ID No. 2 or SEQ ID No. 3, and preferably at least 80% and particularly preferably at least 90% to 95% identical to the polypeptide according to SEQ ID No. 2 or SEQ ID No. 3 and that have the aforementioned activity.

The present invention furthermore relates to a process for the fermentative production of amino acids selected from the group comprising L-asparagine, L-threonine, L-serine, L-glutamate, L-glycine, L-alanine, L-cysteine, L-valine, L-methionine, L-isoleucine, L-leucin, L-tyrosine, L-phenylalanine, L-histidine, L-lysine, L-tryptophan and L-arginine, in particular L-lysine and L-glutamate, using coryneform bacteria that in particular already produce the aminc acids, especially L-lysine and/or L-glutamate, and in which the nucleotide sequences coding for the sucC- and/or sucD-gene are attenuated, and in particular are expressed at a low level.

The term "attenuation" describes in this connection the reduction or switching off of the intracellular activity of one or more enzymes (proteins) in a microorganism that can be coded by the corresponding DNA, by for example using a weak promoter or a gene and/or allele that codes for a corresponding enzyme with a low activity and/or inactivates the corresponding gene and/or allele or enzyme (protein) and optionally combines these features.

The microorganisms that are the subject of the present invention can produce amino acids, in particular L-lysine, from glucose, sucrose, lactose, fructose, maltose, molasses, starch, cellulose or from glycerol and ethanol. The microorganisms may be types of coryneform bacteria, in particular of the genus Corynebacterium. In the genus Corynebacterium there should in particular be mentioned the type Corynebacterium glutamicum, which is known to those skilled in the art for its ability to produce L-amino acids.

Suitable strains of the genus Corynebacterium, in particular of the type Corynebacterium glutamicum, are in particular the following known wild type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and mutants and/or strains obtained therefrom that produce L-amino acids, such as for example the L-lysine-producing strains:

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM 5714.

The new genes sucC and sucD coding for the enzyme succinyl-CoA synthetase (EC 6.2.1.5) have been isolated from *C. glutamicum*.

In order to isolate the sucC- and/or the sucD-gene or also other genes from *C. glutamicum*, a gene library of this microorganism is first of all cultivated in *E. coli*. The cultivation of gene libraries is described in generally known textbooks and handbooks. By way of example there may be mentioned the textbook by Winnacker: Gene und Klone, Eine Einfuthrung in die Gentechnologie (Verlag Chemie, Weinheim, Germany, 1990) or the handbook by Sambrook et al.: Molecular Cloning, A Laboratory Manual (Cold Spring Harbor Laboratory Press, 1989). A very well-known gene library is that of the *E. coli* K-12 strain W3110, which has been cultivated by Kohara et al. (Cell 50, 495–508 (1987)) in λ-vectors. Bathe et al. (Molecular and General Genetics, 252:255–265, 1996) describe a gene library from *C. glutamicum* ATCC13032 that has been cultivated with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326 (1992)) in turn describe a gene library obtained from *C. glutamicum* ATCC13032 using the cosmid pHC79 (Hohn and Collins, Gene 11, 291–298 (1980)). O'Donohue (The Cloning and Volecular Analysis of Four Common Aromatic Amino Acid Biosynthetic Genes from *Corynebacterium glutamicum*. Ph.D. Thesis, National University of Ireland, Galway, 1997) describes the cloning of *C. glutamicum* genes using the λ Zap Expression system described by Short et al. (Nucleic Acids Research, 16: 7583).

In order to produce a gene library from *C. glutamicum* in *E. coli*, plasmids such as pBR322 (Bolivar, Life Sciences, 25, 807–818 (1979)) or pUC9 (Vieira et al., 1982, Gene, 19:259–268) may also be used. Particularly suitable as hosts are those *E. coli* strains that are restriction-defective and recombinant-defective, such as for example the strain DH5α (Jeffrey H. Miller: "A Short Course in Bacterial Genetics, A Laboratory Manual and Handbook for *Escherichia coli* and Related Bacteria", Cold Spring Harbour Laboratory Press, 1992).

The long DNA fragments cloned with the aid of cosmids or other λ-vectors may then in turn be sub-cloned into accessible vectors suitable for DNA sequencing.

Methods for DNA sequencing are described inter alia by Sanger et al. (Proceedings of the National Academy of Sciences of the United States of America, 74:5463–5467, 1977).

The DNA sequences that are obtained may then be investigated with known algorithms and/or sequence analysis programs, such as for example that of Staden (Nucleic Acids Research 14, 217–232(1986)), the GCG-program of Butler (Methods of Biochemical Analysis 39, 74–97 (1998)), the FASTA algorithm of Pearson and Lipman (Proceedings of the National Academy of Sciences USA 85,2444–2448 (1988)) or the BLAST algorithm of Altschul et al. (Nature Genetics 6, 119–129 (1994)) and compared with the sequence entries listed in publicly accessible data banks. Publicly accessible data banks for nucleotide sequences are for example those of the European Molecular Biologies Laboratories (EMBL, Heidelberg, Germany) or those of the Naticnal Center for Biotechnology Information (NCBI, Bethesda, Md., USA).

The rew DNA sequences of *C. glutamicum* coding for the sucC- and sucD-genes have been discovered, and as SEQ ID No. 1 are part of the present invention. The amino acid sequence of the corresponding proteins has furthermore been derived from the existing DNA sequences using the methods described above. The resultant amino acid sequences of the sucC- and sucD-gene product are shown in SEQ ID No. 2 and SEQ ID No. 3.

Coding DNA sequences that arise from SEQ ID No. 1 due to the degeneracy of the genetic code are also a subject of the invention. In the same way DNA sequences that hybridize with SEQ ID No. 1 or parts of SEQ ID No. 1 are a subject of the invention. Finally, DNA sequences that are produced by the polymerase chain reaction (PCR) using primers obtained from SEQ ID No. 1 are also the subject of the invention.

The person skilled in the art will find information on identifying DNA sequences by means of hybridization in, inter alia, the handbook "The DIG System User's Guide for Filter Hybridization" published by Boehringer Mannheim GmbH (Mannheim, Germany, 1993) and in Liebl et al. (International Journal of Systematic Bacteriology (1991) 41: 255–260). The hybridization takes place under stringent conditions, in other words only hybrids are formed in which the probe and target sequence, i.e. the polynucleotides treated with the probe, are at least 70% identical. It is known that the thoroughness of the hybridization including the washing stages is influenced or even determined by varying the buffer composition, temperature and the salt concentration. The hybridization reaction is preferably carried out at a relatively low degree of thoroughness compared to the washing stages (Hybaid Hybridisation Guide, Hybaid Limited, Teddington, UK, 1996).

A 5×SSC-buffer for example may be used at a temperature of ca. 50–68° C. for the hybridization reaction. In this connection probes may also be hybridized with polynucleotides that have less than 70% identity with the sequence of the probe. Such hybrids are less stable and are removed by washing under stringent conditions. This may be effected for example by reducing the salt concentration to 2×SSC and optionally subsequently to 0.5×SSC (The DIG System User's Guide for Filter Hybridization, Boehringer Mannheim, Mannheim, Germany, 1995), a temperature of ca. 50–68° C. being maintained. It is also optionally possible to reduce the salt concentration down to 0.1×SSC. By stepwise raising of the hybridization temperature in steps of ca. 1–2° C. from 50 to 68° C., polynucleotide fragments can be separated that exhibit for example at least 70% or at least 80% or at least 90% to 95% identity to the sequence of the probe that is used. Further instructions for hybridization are available on the market in the form of so-called kits (e.g. DIG Easy Hyb von der Firma Roche Diagnostics GmbH, Mannheim, Germany, Catalog No. 1603558).

The parson skilled in the art can find details of the enhancement of DNA sequences by means of the polymerase chain reaction (PCR) in, inter alia, the handbook by Gait: Oligonucleotide synthesis: A Practical Approach (IRL Press, Oxford, UK, 1984) and in Newton and Graham: PCR (Spektrum Akademischer Verlag, Heidelberg, Germany, 1994).

It has now been found that coryneform bacteria produce L-amino acids, in particular L-lysine, in an improved manner after attenuation of the succ- and/or sucD-gene.

In order to achieve such an attenuation, either the expression of the sucC- and/or sucD-gene or the catalytic properties of the enzyme proteins can be reduced or switched off. Both measures may optionally be combined.

The reduction of the gene expression may be achieved by suitable culture conditions or by genetic alteration (mutation) of the signal structures of the gene expression. Signal structures of the gene expression are for example repressal genes, activator genes, operators, promoters, attenuators, ribosone bonding sites, the start codon and terminators. The person skilled in the art can find information on the above in for example patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Patek et al. (Microbiology 142: 1297 (1996)) and in known textbooks on genetics and molecular biology, such as for example the textbook by Knippers ("Molekulare Genetik", 6$^{th}$ Edition, Georg Thieme Verlag, Stuttgart, Germany, 1995) or the textbook by Winnacker ("Gene und Klone", VCH Verlagsgesellschaft, Weinheim, Germany, 1990).

Mutations that lead to an alteration and/or reduction of the catalytic properties of enzyme proteins are known in the prior art; there may be mentioned by way of example the work carried out by Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus *Corynebacterium glutamicum*: Aufhebung der allosterischen Regulation und Struktur des Enzyms", reports of the Juilichs Research Center, Jül-2906, ISSN09442952, Jülich, Germany, 1994). Overviews and summaries may be obtained from known textbooks on genetics and molecular biology, such as for example those by Hagemann ("Allgemeine Genetik", Gustav Fischer Verlag, Stuttgart, 1986).

Mutations cover such phenomena as transitions, transversions, insertions and deletions. Depending on the effect of the amino acid exchange on the enzyme activity, one speaks of missense mutations or nonsense mutations. Insertions or deletions of at least one base pair in a gene lead to frame shift mutations, as a result of which false amino acids are incorporated or the translation is prematurely arrested. Deletions of several codons typically lead to a complete suppression of the enzyme activity. Details of producing such mutations are part of the prior art and can be obtained from known textbooks on genetics and molecular biology, such as for example the textbook by Knippers ("Molekulare Genetik", 6$^{th}$ Edition, Georg Thieme Verlag, Stuttgart, Germany, 1995), that by Winnacker ("Gene und Klone", VCH Verlagsgesellschaft, Weinheim, Germany, 1990) or that by Hagemann ("Allgemeine Genetik", Gustav Fischer Verlag, Stuttgart, 1986).

A conventional method of mutating genes of *C. glutamicum* is the method of gene disruption and gene replacement described by Schwarzer and Puhler (Bio/Technology 9, 84–87 (1991)).

In the method of gene disruption a central part of the coding region of the gene that is of interest is cloned in a plasmid vector that can replicate in a host (typically *E. coli*), but not in *C. glutamicum*. Vectors that may be used include for example pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega Corporation, Madison, Wiss., USA), pCR2.1-TOPO (Shuman (1994). Journal of Biological Chemistry 269:32678–84; U.S. Pat. No. 5,487,993), pCR®Blunt (Firma Invitrogen, Groningen, Niederlande; Bernard et al., Journal of Molecular Biology, 234: 534–541 (1993)) or pEM1 (Schrumpf et al, 1991, Journal of Bacteriology 173:4510–4516). The plasmid vector that contains the central part of the coding region of the gene is then converted by conjugation or transformation into the desired strain of *C. glutamicum*.

The method of conjugation is described for example in Schäfer et al. (Applied and Environmental Microbiology 60, 756–759 (1994)). Methods for transformation are described for example in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a crossover event, the coding region of the affected gene is disrupted by the vector sequence and two incomplete alleles are obtained, each of which lacks the 3'- and the 5'-end. This method has been used for example by Fitzpatrick et al. (Applied Microbiology and Biotechnology 42, 575–580 (1994)) in order to switch off the recA-gene of C. glutamicum. The sucC- and/or sucD-gene may be switched off in this way.

In the method of gene replacement a mutation, such as for example a deletion, insertion or base exchange is produced in vitro in the gene that is of interest. The allele that is produced is in turn cloned in a vector that is not replicative for C. glutamicum and the vector is then converted by transformation or conjugation into the desired host for C. glutamicum. The incorporation of the mutation and/or of the allele in the target gene and/or in the target sequence is achieved after homologous recombination by means of a first crossover event effecting integration and an appropriate second crossover event effecting excision. This method has been used for example by Peters-Wendisch (Microbiology 144, 915–927 (1998)) in order to switch off the pyo-gene of C. glutamicum by means of a deletion. A deletion, insertion or a base exchange can be incorporated into the sucC- and/or sucD-gene in this way.

A deletion, insertion or a base exchange can be incorporated into the sucC- and/or sucD-gene in this way.

Furthermore, it was found that by means of one or more amino acid replacements in the succ-protein (SEQ ID No. 2) selected from the group: replacement at position 22 by any other proteinogenic amino acid except L-proline, replacement at position 44 by any other proteinogenic amino acid except glycine, and replacement at position 170 by any other proteinogenic amino acid except L-alanine, an attenuation takes place and coryneform bacteria that carry the corresponding amino acid replacement produced amino acids in an improved way, in particular L-lysine and/or L-glutamic acid.

Particularly preferred are one or more amino acid replacements selected from the group: L-proline at position 22 by L-serine, glycine at position 44 by L-glutamic acid, and L-alanine at position 170 by L-threonine.

Most particularly preferred is an SucC-protein that contains L-serine at position 22, L-glutamic acid at position 44, and L-threonine at position 170, as shown in SEQ ID No. 5.

As shown in SEQ ID No. 4 the replacement of L-proline by L-threonine at position 22 of the amino acid sequence may preferably be effected by replacing the nucleobase cytosine at position 64 by thymine, the replacement of glycine by L-glutamic acid at position 44 of the amino acid sequence may preferably be effected by replacing the nucleobase guanine at position 131 by adenine, and the replacement of L-alanine by L-threonine at position 170 of the amino acid sequence may preferably be effected by replacing the nucleobase guanine at position 508 by adenine.

Conventional mutagenesis methods may be employed for the mutagenesis, using mutagenic agents such as for example N-methyl-N'-nitro-N-nitrosoguanidine or ultraviolet light.

Furthermore, in vitro methods may be used for the mutagenesis, such as for example a treatment with hydroxylamine (J. H. Miller: A Short Course in Bacterial Genetics, Cold Spring Harbor Laboratory Press, Cold Spring Harbor, 1992) or mutagenic oligonucleotides (T. A. Brown: Gentechnologie für Einsteiger, Spektrum Akademischer Verlag, Heidelberg, 1993) or the polymerase chain reaction (PCR), as described in the handbook by Newton and Graham (PCR, Spektrum Akademischer Verlag, Heidelberg, 1994).

The corresponding sucC alleles and genes are sequenced and incorporated into suitable hosts by for example the method of gene replacement.

The present invention accordingly also provides coryneform bacteria containing the SucC proteins, in which the amino acid sequence shown in SEQ ID No. 2 contain one or more replacements selected from the group: replacement at position 22 by any other proteinogenic amino acid except L-proline, replacement at position 44 by any other proteinogenic amino acid except glycine, and replacement at position 170 by any other proteinogenic amino acid except L-alanine.

The invention accordingly furthermore provides polynucleotide sequences derived from coryneform bacteria that contain the genes or alleles coding for the aforementioned SucC proteins.

Furthermore it may be advantageous for the production of L-amino acids, in particular L-lysine, in addition to enhance, in particular to over-express, one or more enzymes of the relevant biosynthesis pathway, glycolysis, anaplerosis, citric acid cycle or amino acid export, in order to attenuate the sucC- and/or sucD-gene.

The expression "enhancement" describes in this connection increasing the intracellular activity of one or more enzymes (proteins) in a microorganism that are coded by the corresponding DNA, by for example increasing the number of copies of the gene or genes or alleles, using a strong promoter or a gene or allele that codes with a high degree of activity for a corresponding enzyme (protein), and optionally combining these measure.

Thus, in the production of L-lysine and/or L-glutamate, in addition to the attenuation of the sucC- and/or sucD-gene, one or more of the genes selected from the following group may be enhanced, in particular over-expressed:

the dapA-gene coding for dihydrodipicolinate-synthase (EP-B 0 197 335), the gap-gene coding for glyceraldehyde-3-phosphate dehydrogenase (Eikmanns (1992), Journal of Bacteriology 174:6076–6086), the gene tpi coding for triosephosphate isomerase (Eikmanns (1992), Journal of Bacteriology 174:6076–6086), the gene pgk coding for 3-phosphoglycerate kinase (Eikmanns (1992), Journal of Bacteriology 174:6076–6086), the pyo-gene coding for pyruvate carboxylase (Eikmanns (1992), Journal of Bacteriology 174:6076–6086), the mqo-gene coding for malate:quinone oxidoreductase (Molenaar et al., European Journal of Biochemistry 254, 395–403 (1998)), the gene lysC coding for a feed-back resistant aspartate kinase (EP-B-0387527; EP-A-0699759; WO 00/63388)), the lysE-gene coding for the L-lysine-export (DE-A-195 48 222), the gene zwal coding for the Zwal-protein (DE: 19959328.0, DSM 13115).

Moreover, it may be advantageous for the production of L-lysine and/or L-glutamate, in addition to the attenuation of the sucC- and/or sucD-gene, at the same time to attenuate, in particular to reduce the expression of one or more of the genes selected from the group comprising:

the gene pgk coding for phosphoenolpyruvate-carboxykinase (DE 199 50 409.1, DSM 13047), the gene pgi coding for glucose-6-phosphate isomerase (US 09/396,478, DSM 12969), the gene poxB coding for pyruvate-oxidase (DE:1995 1975.7, DSM 13114), the gene zwa2 coding for the zwa2-protein (DE: 19959327.2, DSM 13113).

Furthermore it may be advantageous for the production of amino acid, in particular L-lysine and/or L-glutamate, in addition to the attenuation of the suoC- and/or sucD-gene to switch off undesirable secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms containing the polynucleotide according to claim 1 are also the subject of the invention and may be cultured continuously or batchwise in a batch process (batch cultivation) or in a fed batch or repeated fed batch process in order to produce L-amino acids, in particular L-lysine. An overview of known cultivation methods is given in the textbook by Chmiel (Bioprozesstechnik 1. Einfuhrung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must suitably satisfy the demands of the relevant strains. Descriptions of culture media for various microorganisms are given in the handbook "Manual of Methods for General Bacteriology" of the American Society for Bacteriology (Washington D.C., USA, 1981).

As carbon source there may be used sugars and carbohydrates such as for example glucose, sucrose, lactose, fructose, maltose, molasses, starch and cellulose, oils and fats such as for example soya bean oil, sunflower oil, groundnut oil and coconut oil, fatty acids such as for example palmitic acid, stearic acid and linoleic acid, alcohols such as for example glycerol and ethanol, and organic acids such as for example acetic acid. These substances may be used individually or as a mixture.

As nitrogen source there may be used organic nitrogen-containing compounds such as peptones, yeast extract, meat extra-ct, malt extract, corn steep liquor, soya bean flour and urea, or inorganic compounds such as ammonium sulfate, ammonium chloride, ammonium phosphate, ammonium carbonate and ammonium nitrate. The nitrogen sources may be used individually or as a mixture.

As phosphorus source there may be used phosphoric acid, potassium dihydrogen phosphate or dipotassium hydrogen phosphate, or the corresponding sodium-containing salts. The culture medium must furthermore contain salts of metals such as for Example magnesium sulfate or iron sulfate that are necessary for growth. Finally, essential growth substances such as amino acids and vitamins may, in addition to the substances mentioned above, be used. Apart from this, suitable precursors may be added to the culture medium. The aforementioned feedstock substances may be added to the culture in the form of a one-off addition, or may be metered in during the actual cultivation in a suitable way.

Alkaline compounds such as sodium hydroxide, potassium hydroxide, ammonia or ammonia water or acidic compounds such as phosphoric acid or sulfuric acid may be used in an appropriate manner in order to regulate the pH of the culture. Antifoaming agents such as for example fatty acid polyclycol esters may be used to prevent foam formation. Suitable selectively acting substances such as for example antibiotics may be added to the medium in order to maintain the stability of plasmids. Oxygen or oxygen-containing gas mixtures such as for example air are introduced into the culture in order to maintain aerobic conditions. The temperature of the culture is normally 20° C. to 45° C. and preferably 25° C. to 40° C. The culture is continued until a maximum yield of the desired product has been formed. This target is normally achieved within 10 hours to 160 hours.

A pure culture of the strain *Escherichia coli* DH5αmar/pK18mobsacBsucDdel was filed according to the Budapest Convention on Sept. 29, 2000 as DSM 13749 at the CGerman Collection for Microorganisms and Cell Cultures (DSMZ, Brunswick, Germany).

A pure culture of the strain *Escherichia coli* Top10/pCRBluntsucCint was filed according to the Budapest Convention on Sept. 29, 2000 as DSM 13750 at the German Collection for Microorganisms and Cell Cultures (DSMZ, Brunswick, Germany).

Methods for determining L-amino acids are known from the prior art. The analysis may be carried out as described for example by Spackman et al. (Analytical Chemistry, 30, (1958), 1190) by anion exchange chromatography followed by ninhydrin derivatisation or may be carried out by reverse phase HPLC, as described by Lindroth et al. (Analytical Chemistry (1979) 51: 1167–1174).

The present invention is described in more detail hereinafter with the aid of embodiments.

EXAMPLE 1

Production of a Genomic Cosmid Gene Library from *Coryrebacterium glutamicum* ATCC 13032

Chromosomal DNA from *Corynebacterium glutamicum* ATCC 13032 was isolated as described by Tauch et al. (1995, Plasmid 33:168–179) and partially cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987) Proceedings of the National Academy of Sciences, USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase. The cosmid-DNA was then cleaved with the restriction enzyme BamHI (Amersham Pharmacia, Freiburg, Germany, Product Description BamHI, Code no. 27-0868-04). The cosmid-DNA treated in this way was mixed with the treated ATCC13032-DNA and the batch was treated with T4-DNA-ligase (Amersham Pharmacia, Freiburg, Germany, Product Description T4-DNA-ligase, Code no. 27-0870-04). The ligation mixture was then packed in phages with the aid of the Gigapack II XL Packing Extracts (Stratagene, La Jolla, USA, Product Description Gigapack II XL Packing Extract, Code no. 200217). In order to infect the *E. coli* strain NM554 (Raleigh et al. 1988, Nucleic Acid Res. 16:1563–1575) the cells were taken up in 10 mM $MgSO_4$ and mixed with an aliquot of the phage suspension.

Infection and titration of the cosmid bank were carried out as described by Sambrook et al. (1989, Molecular Cloning: A Laboratory Manual, Cold Spring Harbor), the cells having been plated out on LB-agar (Lennox, 1955, Virology, 1:190) with 100 μg/ml ampicillin. Recombinant individual clones were selected after incubation overnight at 37° C.

EXAMPLE 2

Isolation and Sequencing of the genes sucC and sucD

The cosmid-DNA of an individual colony was isolated using the Qiaprep Spin Miniprep Kit (Product No. 27106, Qiagen, Hilden, Germany) according to the manufacturers instructions and partially cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250).

After gel electrophoresis separation the cosmid fragments were isolated in the large region from 1500 to 2000 bp using the QiaExII Gel Extraction Kit (Product No. 20021, Qiagen, Hilden, Germany). The DNA of the sequencing vector pZero-1 obtained from Invitrogen (Groningen, Niederlande, Product Description Zero Background Cloning Kit, Product No. F2500-01) was cleaved with the restriction enzyme BamHI (Amersham Pharmacia, Freiburg, Germany, Product Description BamHI, Product No. 27-0868-04). The ligation of the cosmid fragments in the frequencing vector pZero-1 was carried out as described by Sambrook et al. (1989, Molecular Cloning: A Laboratory Manual, Cold Spring Harbor), the DNA mixture having been incubated overnight with T4-ligase (Pharmacia Biotech, Freiburg, Germany). This ligation mixture was electroporated into the *E. coli* strain DH5αMCR (Grant, 1990, Proceedings of the National Academy of Sciences U.S.A., 87:4645–4649) (Tauch et al. 1994, FEMS Microbiol Letters, 123:343–7) and was plated out on LE-agar (Lennox, 1955, Virology, 1:190) with 50 µg/ml zeocin. The plasmid preparation of the recombinant clones was performed with Biorobot 9600 (Product No. 900200, Qiagen, Hilden, Germany). The sequencing was carried out according to the dideoxy chain termination method of Sanger et al. (1977, Proceedings of the National Academies of Sciences U.S.A., 74:5463–5467) as modified by Zimmermann et al. (1990, Nucleic Acids Research, 18:1067). The RR dRhodamin Terminator Cycle Sequencing Kit from PE Applied Biosystems(Product No. 403044, Weiterstadt, Germany) was used. The gel electrophoresis separation and analysis of the sequencing reaction was performed in a rotiphoresis NF acrylamide/bisacrylamide gel (29:1) (Product No. A124.1, Roth, Karlsruhe, Germany) together with the "ABI Prism 377" sequencing equipment from PE Applied Biosystems (Weiterstadt, Germany).

The raw sequence data that were obtained were then processed using the Staden program package (1986, Nucleic Acids. Research, 14:217–231) Version 97-0. The individual sequences of the pzero1 derivates were assembled into a coherent Contig. The computer-assisted analysis of the coding region was performed with the program XNIP (Staden, 1986, Nucleic Acids Research, 14:217–231). Further analyses were carried out with the BLAST search programs (Altschul et al., 1997, Nucleic Acids Research, 25:3389–3402), against the non-redundant data bank of the National Center for Biotechnology Information (NCBI, Bethesda, Md., USA).

The nucleotide sequence that was obtained is illustrated in SEQ ID No. 1. Analysis of the nucleotide sequence showed an open reading frame of 1206 base pairs, which was identified as sucC-gene, as well as an open reading frame of 882 base pairs, identified as sucD. The succ-gene codes for a polypeptide of 402 amino acids, which is shown in SEQ ID NO. 2. The sucD-gene codes for a polypeptide of 294 aminc acids, which is shown in SEQ ID No. 3.

EXAMPLE 3

3.1 Production of an Integration Vector for the Integration Mutagenesis of the sucC-Gene Chromosomal DNA was isolated from the strain ATCC 13032 according to the method of Eikmanns et al. (Microbiology 140: 1817–1828 (1994)). On the basis of the sequence of the succ-gene for *C. glutamicum* known from Example 1 the following oligonucleotides were selected for the polymerase chain reaction (see SEQ ID No. 6 and SEQ ID No. 7):

primer sucC-in1:
   5'CGC GCG AAT CGT TCG TAT 3'
primer sucC-in2:
   5'CGC CAC CAA TGT CTA GGA 3'

The indicated primers were synthesised by MWG Biotech (Ebersberg, Germany) and the PCR reaction was carried out with the Pwo polymerase from Boehringer Mannheim (Germany, Product Description Pwo DNA Polymerase, Product No. 1 644 947) according to the standard PCR method of Innis et al. (PCR Protocols. A Guide to Methods and Applications, 1990, Academic Press). With the aid of the polymerase chain reaction the primers permit the enhancement of an approximately 0.55 kb large internal fragment of the sucC-gene. The product enhanced in this way was checked by electrophoresis in a 0.8% agarose gel.

The enhanced DNA fragment was ligated into the vector pCR®Blunt II (Bernard et al., Journal of Molecular Biology, 234: 534–541 (1993)) using the Zero Blunt™ Kit from Invitrogen Corporation (Carlsbad, Calif., USA; Catalogue Number K2700-20).

The *E. coli* strain TOP10 was then electroporated into the ligation batch (Hanahan, In: DNA Cloning. A Practical Approach, Vol. I, IRL-Press, Oxford, Washington D.C., USA, 1985). The selection of plasmid-carrying cells was performed by plating out the transformation batch onto LB agar (Sambrook et al., Molecular Cloning: A Laboratory Manual, $2^{nd}$ Ed., Cold Spring Harbor Laboratory Press, Cold Spring Harbor, N.Y., 1989) that had been supplemented with 25 mg/l of kanamycin. Plasmid DNA was isolated from a transformant with the aid of the QIAprep Spin Miniprep Kit from Qiagen and checked by restriction with the restriction enzyie EcoRI followed by agarose gel electrophoresis (0,8%). The plasmid was named pCRBluntsucCint and is shown in FIG. 1.

3.2 Deletion of the sucD-gene

For this purpose chromosomal DNA was isolated from the strain ATCC13032 by the method of Tauch et al. (1995, Plasmid 33:168–179). On the basis of the sequence of the sucD-gene for *C. glutamicum* known from Example 2 the oligcnucleotides described hereinafter were selected for producing the sucD deletion allele (see SEQ ID No. 8 to SEQ ID No. 11):
primer sucD-d1:
   5'-CGA TGT GAT TGC GCT TGA TG-3'
deletion primer sucD-d2:
   5'-ACC TCA CGC ATA AGC TTC GCA TGC TCT GAA CCT TCC GAA C-3'
deletion primer sucD-d3:
   5'-GTT CGG AAG GTT CAG AGC ATG CGA AGC TTA TGC GTG AGG T-3'
primer sucD-d4:
   5'-ATG AAG CCA GCG ACT GCA GA-3'

The relevant primers were synthesised by MWG Biotech (Ebersberg, Germany) and the PCR reaction was carried out using the Pfu polymerase (Stratagene, Product. No. 600135, La Jolla, USA) and the PTC 100-Thermocyclers (MJ Research Inc., Waltham, USA). With the aid of the polymerase chain reaction the primers permit the enhancement of a sucD allele with internal deletion. The product enhanced in this way was tested by electrophoresis in a 0.8% agarose gel and was also sequenced as described by Sanger et al. (Proceedings of the National Academy of Sciences of the United States of America, 74:5463–5467, 1977).

EXAMPLE 4

4.1 Integration mutagenesis of the succ-gene in the strain DSM 5715

The vector pCRBluntsucCint mentioned in Example 3.1 was electroporated into C. glutamicum DSM 5715 (EP 0 435 132) according to the electroporation method of Tauch et. al. (FEMS Microbiological Letters, 123:343–347 (1994)). The strain DSM 5715 is an AEC resistant L-lysine producer. The vector pCRBlunt-sucCint cannot independently replicate in DSM5715 and accordingly only remains in the cellulose if it had integrated into the chromosome of DSM 5715. The selection of clones with pCRBluntsucCint integrated into the chromosome is performed by plating out the electroporation batch onto LB agar (Sambrook et al., Molecular Cloning: A Laboratory Manual, $2_{nd}$ Ed., Cold Spring Harbor Laboratory Press, Cold Spring Harbor, N.Y.) that had been supplemented with 15 mg/l of kanamycin.

In order to detect the integration the sucCint fragment was labelled according to the method described in "The DIG System User's Guide for Filter Hybridization" of Boehringer Mannheim GmbH (Mannheim, Germany, 1993) using the Dig-Hybridization Kit from Boehringer. Chromosomal DNA of a potertial integrant was isolated according to the method of Eikmanns et al. (Microbiology 140: 1817–1828 (1994)) and was cut in each case with the restriction enzyme SphI and HindIII. The resultant fragments were separated by means of acarose gel electrophoresis and hybridized at 68° C. using the Dig-Hybridization Kit from Boehringer. The plasmid pCRBluntsucCint named in Example 3.1 had inserted itself into the chromosome of DSM5715 within the chromosomal sucC-gene. The strain was identified as DSM5715:: pCRBluntsucCint.

4.2 Construction of the Exchange Vector pK18mobsacBsucDdel

The sucD-deletion derivative obtained in Example 3.2 was, after separation in an agarose gel (0.8%) using the Qiagenquick Gel Extraction Kit (Qiagen, Hilden, Germany), isolated from the agarose gel and then used with the mobilisable cloning vector pK18mobsacB (Schafer et al. (1994), Gene 14: 69–73) for the ligation. This had previously been cleaved with the restriction enzymes XmaI-and YbaI, mixed with the sucD-deletion allele, and treated with T4-DNA-ligase (Amersham Pharmacia, Freiburg, Germany).

The E. coli strain DH5αmcr (Grant, 1990, Proceedings of the National Academy of Sciences U.S.A., 87:4645–4649) was then electroporated with the ligation batch (Hanahan, In. DNA Cloning. A Practical Approach, Vol.1, ILR-Press, Cold Spring Harbor, N.Y., 1989). The plasmid-carrying cells were selected by plating out the transformation batch onto LB agar(Sambrock et al., Molecular Cloning: A Laboratory Manual. $2^{nd}$ Ed. Cold Spring Harbor, N.Y., 1989) that had been supplemented with 25 mg/l of kanamycin.

Plasmid DNA was isolated from a transformant by means of the QIAprep Spin Miniprep Kit from Qiagen, and the cloned sucD-deletion allele was verified by means of sequencing by the company MWG Biotech (Ebersberg, Germany). The plasmid was named pK18mobsacBsucDdel. The strain was identified as E.coli DH5αmcr/pK18mobsacBsucDdel.

4.3 Deletion Mutagenesis of the sucD-Gene in the C. Glutamicum Strain DSM 5715

The vector pK18mobsacBsucDdel mentioned in Example 4.2 was electroporated according to the electroporation method of Tauch et al.,(1989 FEMS Microbiology Letters 123: 343–347). The vector cannot replicate independently in DSM 5715 and accordingly only remains in the cellulose if it has integrated into the chromosome. The selection of clones with integrated pK18mobsacBsucDdel was performed by plating out the electroporation batch onto LB-agar (Sambrock et al., Molecular Cloning: A Laboratory Manual, $2^{nd}$ Ed., Cold Spring Harbor, N.Y., 1989) that had been supplemented with 15 mg/l of kanamycin. Cultivated clones were streaked out onto LB-agar plates containing 25 mg/l of kanamycin and incubated for 16 hours at 33° C.

In order to achieve the excision of the plasmid together with the complete chromosomal copy of the sucD-gene, the clones were then grown on LB-agar containing 10% sucrose. The plasmid pK18mobsacB contains a copy of the sacB-gene, which converts sucrose into levansucrase that is not toxic for C. glutamicum. Accordingly only those clones in which the integrated pK18mobsacBsucDdel has in turn been excised can be grown on LB-agar containing sucrose. In the excision either the complete chromosomal copy of the sucD-gene or the incomplete copy together with the internal deletion can be excised together with the plasmid.

In order to detect whether the incomplete copy of sucD still remains in the chromosome, the plasmid pK18mobsacBsucDdel fragment was labelled according to the method described in "The DIG System Users Guide for Filter Hybridization" published by Boehringer Mannheim GmbH (Mannheim, Germany, 1993) using the Dig-Hybridization Kit from Boehringer. Chromosomal DNA of a potential deletion mutant was isolated according to the method of Eikmanns et al. (Microbiology 140: 1817–1828 (1994)) and was in each case cut into separate sections using the restriction enzymes SphI and PstI. The resultant fragments were separated by agarose gel electrophoresis and hybridized at 68° C. using the Dig Hybridization Kit from Boehringer. On the basis of the resultant fragments it could be shown that the strain DSM5715 has lost its complete copy of the sucD-gene and instead only the deleted copy is still available.

The strain was identified as C. glutamicum DSM5715ΔsucD.

EXAMPLE 5

5.1 Production of L-Glutamate Using the Strain DSM 5715::pCRBluntsucCint

The C. glutamicum strain DSM5715::pCRBluntsucCint obtained in Example 4.1 was cultivated in a suitable nutrient medium for producing L-glutamate and the glutamate content in the culture supernatant was determined.

For this purpose the strain was first of all incubated for 24 hours at 33° C. on agar plates with the corresponding antibiotic (brain-heart agar with kanamycin (25 mg/l). A pre-culture was inoculated using this agar plate culture (10 ml of medium in a 100 ml Erlenmeyer flask). The full medium Cg III was used as medium for the pre-culture.

| Medium Cg III | |
|---|---|
| NaCl | 2.5 g/l |
| Bacto-Peptone | 10 g/l |
| Bacto-Yeast Extract | 10 g/l |

-continued

| Medium Cg III | |
|---|---|
| Glucose (separately autoclaved) | 2% (w/v) |
| The pH was adjusted to pH 7.4 | |

Kanamycin (25 mg/l) was added to this medium. The pre-culture was incubated on a shaker for 16 hours at 33° C. at 240 rpm. A main culture was inoculated from this pre-culture so that the initial optical density (660 nm) of the main culture was 0.1 OD. The medium MM was used for the main culture.

| Medium MM | |
|---|---|
| CSL (Corn Steep Liquor) | 5 g/l |
| MOPS (Morpholinopropanesulfonic acid) | 20 g/l |
| Glucose (separately autoclaved) | 50 g/l |
| Salts: | |
| $(NH_4)_2SO_4)$ | 25 g/l |
| $KH_2PO_4$ | 0.1 g/l |
| $MgSO_4.7H_2O$ | 1.0 g/l |
| $CaCl_2.2H_2O$ | 10 mg/l |
| $FeSO_4.7H_2O$ | 10 mg/l |
| $MnSO_4.H_2O$ | 5.0 mg/l |
| Biotin (sterile filtered) | 0.3 mg/l |
| Thiamine.HCl (sterile filtered) | 0.2 mg/l |
| Fumarate (sterile filtered) | 5.81 g/l |
| Leucine (sterile filtered) | 0.1 g/l |
| $CaCO_3$ | 25 g/l |

CSL, MOPS and the salt solution are adjusted with ammonia water to pH 7 and autoclaved. The sterile substrate and vitamin solutions as well as the dry autoclaved $CaCO_3$ are then added.

Cultivation takes place in a 10 ml volume in a 100 ml Erlenmeyer flask with baffles. Kanamycin (25 mg/l) was added. Cultivation took place at 33° C. and 80% atmospheric humidity.

After 24 hours the OD was measured at a measurement wavelength of 660 nm using the Biomek 1000 instrument (Beckmann Instruments GmbH, Munich). The amount of glutamate formed was measured in an amino acid analyser from Eppendorf-BioTronik (Hamburg, Germany) by ion exchange chromatography and post-column derivatisation with ninhydrin detection.

The result of the test is shown in Table 1.

TABLE 1

| Strain | OD (660 nm) | L-glutamate mg/l |
|---|---|---|
| DSM5715 | 10.4 | 20 |
| DSM5715::pCRBlunt sucCint | 3.9 | 154 |

5.2 Production of L-Glutamate Using the Strain DSM5715ΔsucD

The *C. glutamicum* strain DSM5715/pK18mobsacBsucDdel obtained in Example 4.3 was cultivated in a nutrient medium suitable for producing L-glutamate and the glutamate content in the culture supernatant was measured.

For this purpose the strain was first of all incubated for 24 hours at 33° C. on agar plates. A preculture was inoculated using this agar plate culture (10 ml medium in 100 ml Erlenmeyer flask). The full medium CgIII was used for the preculture. Kanamycin (25 mg/l) was added to this medium. The preculture was incubated on a shaker for 16 hours at 33° C. and at 240 rpm. A main culture was inoculated from this preculture so that the initial OD (660 nm) of the main culture was 0.1 OD. The medium MM was used for the main culture.

The cultivation was carried out in a 10 ml volume in a 100 ml Erlenmeyer flask equipped with baffles. Cultivation was carried out at 33° C. and 80% atmospheric humidity.

After 72 hours the OD was measured at a measurement wavelength of 660 nm using a Biomek 1000 instrument (Beckmann Instruments GmbH, Munich). The amount of gluta-mate formed was measured with an amino acid analyser from Eppendorf-BioTronik (Hamburg, Germany) by ion exchange chromatography and post-column derivatisation with ninhydrin detection.

The result of the test is shown in Table 2.

TABLE 2

| Strain | OD (660 nm) | L-glutamate mg/l |
|---|---|---|
| DSM5715 | 8.1 | 7 |
| DSM5715ΔsucD | 13.3 | 33 |

BRIEF DESCRIPTION OF THE FIGURES

FIG. 1: Map of the plasmid pCRBluntsucCint.

FIG. 2: Map of the plasmid pK18mobsacBsucDdel

The acronyms and abbreviations used in FIG. 1 have the following meanings:

KmR: Kanamycin resistance gene
Zeocin: Zeocin resistance gene
HindIII Cutting site of the restriction enzyme HindIII
SphI Cutting site of the restriction enzyme SphI
EcoRI: Cutting site of the restriction enzyme EcoRI
sucCint: Internal fragment of the sucC-gene
ColE1 ori: Replication origin of the plasmid ColE1

The acronyms and abbreviations used in FIG. 2 have the following meanings:

oriV: ColE1-like origin of pMB1
sacB The sacB-gene coding for the protein levansucrose
RP4mob: RP4-mobilisation site
Kan: Resistance gene for kanamycin
sucDdel': 5'-terminal fragment of the sucD-gene from *C. glutamicum*
sucDdel": 3'-terminal fragment of the sucD-gene from *C. glutamicum*
SphI: Cutting site of the restriction enzyme SphI
PstI: Cutting site of the restriction enzyme PstI
XmaI: Cutting site of the restriction enzyme XmaI
XbaI: Cutting site of the restriction enzyme XbaI

What is claimed is:

1. An isolated polynucleotide comprising the nucleotide sequence of nucleotides 142–1347 of SEQ ID NO:1 and wherein said polynucleotide encodes a protein with succinyl-CoA synthetase enzymatic activity.

2. A vector comprising the polynucleotide of claim 1.

3. The vector of claim 2, wherein said vector is a plasmid.

4. A bacterial host cell transformed with the vector of claim 3.

5. The bacterial host cell of claim 4, wherein said bacterial host cell is of the species *Corynebacterium glutamicum*.

6. An isolated polynucleotide comprising the nucleotide sequence of nucleotides 1372–2253 of SEQ ID NO:1 and wherein said polynucleotide encodes a protein with succinyl-CoA synthetase enzymatic activity.

7. A vector comprising the polynucleotide of any one of claim 6.

8. The vector of claim 7, wherein said vector is a plasmid.

9. A bacterial host cell transformed with the vector of claim 8.

10. The bacterial host cell of claim 9, wherein said bacterial host cell is of the species *Corynebacterium glutamicum*.

11. An isolated polynucleotide consisting of a nucleotide sequence encoding a protein with an amino acid sequence comprising that of SEQ ID NO:2; wherein said SEQ ID NO:2 sequence has one or more of the following amino acid changes:
  a) the proline at position 22 is replaced by another amino acid;
  b) the glycine at position 44 is replaced by another amino acid;
  c) the alanine at position 170 is replaced by another amino acid;
  and wherein said protein has succinyl-CoA synthetase enzymatic activity.

12. An isolated polynucleotide consisting of a nucleotide sequence encoding a protein with an amino acid sequence comprising that of SEQ ID NO:2; wherein said SEQ ID NO:2 sequence has one or more of the following amino acid changes:
  a) the proline at position 22 is replaced by serine;
  b) the glycine at position 44 is replaced by glutamate;
  c) the alanine at position 170 is replaced by threonine;
  and wherein said protein has succinyl-CoA synthetase enzymatic activity.

13. The isolated polynucleotide 12, wherein said SEQ ID NO:2 sequence has been changed such that:
  a) serine is at amino acid position 22;
  b) glutamate is at amino acid position 44;
  c) threonine is at amino acid position 170.

14. An isolated polynucleotide comprising the nucleotide sequence of SEQ ID NO:4 wherein said polynucleotide encodes a protein with succinyl-CoA synthetase enzymatic activity.

15. A vector comprising the polynucleotide of any one of claims 11–14.

16. A bacterial host cell transformed with the vector of claim 15.

17. The bacterial host cell of claim 16 wherein said bacterial host cell is of the species *Corynebacterium glutamicum*.

18. A vector selected from the group consisting of:
  a) the integration vector pCRBluntsucCint as shown in FIG. 1 and which has been deposited in *E. coli* as DSM 13750; and
  b) the vector pK18mobsacBsucDdel as shown in FIG. 2 and which has been deposited in *E. coli* as DSM 13749.

19. A bacterial host cell transformed with the vector of claim 18.

20. The bacterial host cell of claim 19, wherein said bacterial host cell is of the species *Corynebacterium glutamicum*.

* * * * *